(12) United States Patent
Ghosh et al.

(10) Patent No.: US 8,722,881 B2
(45) Date of Patent: May 13, 2014

(54) METHOD OF SYNTHESIS OF TETRADENTATE AMIDE MACROCYCLE LIGAND AND ITS METAL-COMPLEX

(75) Inventors: Anindya Ghosh, Little Rock, AR (US); Shane Z. Sullivan, Redfield, AR (US); Samuel L. Collom, New Haven, CT (US); Sharon Pulla, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 697 days.

(21) Appl. No.: 12/925,053

(22) Filed: Oct. 13, 2010

(65) Prior Publication Data

US 2011/0094043 A1    Apr. 28, 2011

Related U.S. Application Data

(60) Provisional application No. 61/278,880, filed on Oct. 13, 2009.

(51) Int. Cl.
| | | |
|---|---|---|
| *C07D 245/00* | (2006.01) | |
| *C07D 245/04* | (2006.01) | |
| *C07C 45/27* | (2006.01) | |
| *C07F 15/02* | (2006.01) | |
| *C07D 257/10* | (2006.01) | |
| *C07C 291/04* | (2006.01) | |
| *D06L 3/00* | (2006.01) | |
| *D21C 11/00* | (2006.01) | |

(52) U.S. Cl.
USPC ........... 540/460; 540/452; 540/465; 540/470; 540/473; 540/480; 540/482; 252/186.33; 252/186.43; 252/186.39; 562/565; 564/158; 564/298; 564/305; 8/102; 549/518

(58) Field of Classification Search
USPC .......... 252/186.33, 186.43, 186.39; 562/565; 564/158, 298, 305; 8/102; 549/518; 540/452, 460, 465, 470, 473, 480, 482
See application file for complete search history.

(56) References Cited

U.S. PATENT DOCUMENTS

| | | |
|---|---|---|
| 5,847,120 A | 12/1998 | Collins et al. |
| 5,853,428 A | 12/1998 | Collins et al. |
| 5,876,625 A | 3/1999 | Collins et al. |
| 6,011,152 A | 1/2000 | Gordon-Wylie et al. |
| 6,051,704 A | 4/2000 | Gordon-Wylie et al. |
| 6,054,580 A | 4/2000 | Collins et al. |
| 6,099,586 A | 8/2000 | Collins et al. |

(Continued)

OTHER PUBLICATIONS

Article entitled: Design of More Powerful Iron-TAML Peroxidase Enzyme Mimics, by W. Chadwick Ellis et al., published in the J. Am Chem. Soc. 2009, pp. 18052-18053.*

(Continued)

*Primary Examiner* — Joseph D Anthony
(74) *Attorney, Agent, or Firm* — Richard Blakely Glasgow

(57) ABSTRACT

A tetradendate amide based macrocyclic ligand and its Fe(III) complex which act as activators of hydrogen peroxide. The synthetic methodology to develop the ligands is new, simple and provides better yield for each step of the ligand synthesis. The Fe(III)-complexes and hydrogen peroxide together are can perform several environmentally benign oxidation reactions. Organic dye bleaching, bleaching of pulp and paper effluent and N-oxide synthesis may be performed using the newly developed catalyst and hydrogen peroxide. Alcohol oxidation and alkene epoxidation may also be performed using the catalysts and hydrogen peroxide.

8 Claims, 4 Drawing Sheets

1

2

(56) References Cited

U.S. PATENT DOCUMENTS

| | | | |
|---|---|---|---|
| 6,100,394 | A | 8/2000 | Collins et al. |
| 6,136,223 | A | 10/2000 | Collins et al. |
| 6,241,779 | B1 | 6/2001 | Collins et al. |
| 7,060,818 | B2 * | 6/2006 | Horwitz et al. ............... 540/450 |
| 2004/0167329 | A1 | 8/2004 | Horwitz et al. |
| 2011/0094043 | A1 * | 4/2011 | Ghosh et al. ...................... 8/102 |

OTHER PUBLICATIONS

Ellis, W., et al., Designing Green Oxidation Catalysts for Purifying Environmental Waters, J.Am.Chem.Soc., 132, pp. 9774-9781, Jun. 21, 2010.

Sullivan, S., et al., Fe-complex of a tetraamido macrocyclic ligand: Spectroscopic characterization and catalytic oxidation studies, Chemical Physics Letters 498, 359-365, Sep. 6, 2010.

Ellis, W., et al., Design of More Powerful Iron-TAML Peroxidase Enzyme Mimics, J.Am.Chem.Soc. 131, 18052-18053, Nov. 24, 2009.

Ghosh, A., Design, Synthesis and Mechanistic Studies of Iron-TAML Catalytic Activators of Hydrogen Peroxide and a New Activation Chemistry of Dioxygen by Iron, Ph.D. Dissertation, Carnegie Mellon University, Pittsburgh, PA, 2004.

Sen Gupta, S., Iron-TAML® Activators of Hydrogen Peroxide: Synthesis, Characterization and Environmental Applications, Ph.D Dissertation, Carnegie Mellon University, Pittsburgh PA, 2002.

* cited by examiner

| dye ($\lambda_{max}$/nm)[a] | bleaching time/s[b] | |
|---|---|---|
| | pH 10 | PH 11.5 |
| Orange IV (444) | 310 | 305 |
| Clayton Yellow (403) | 307 | 295 |
| Methyl Orange (464) | >600 | >600 |
| Methyl Violet (584) | 235 | 225 |
| Naphthol B Green (718) | 325 | 335 |

| Amine | | Turn over number | % Yield |
|---|---|---|---|
| Pyridine | Catalyst (2) + H$_2$O$_2$ | 407 | 50.8 |
| | H$_2$O$_2$ | - | 22.09 |
| Triethylamine | Catalyst (2) + H$_2$O$_2$ | 667 | 66.67% |
| | H$_2$O$_2$ | - | |
| [a]4-Dimethyl-aminopyridine | Catalyst (2) + H$_2$O$_2$ | - | - |

FIG. 7

METHOD OF SYNTHESIS OF TETRADENTATE AMIDE MACROCYCLE LIGAND AND ITS METAL-COMPLEX

CROSS-REFERENCE TO RELATED APPLICATIONS

This application claims the benefit of U.S. Provisional Patent Application No. 61/278,880 filed Oct. 13, 2010, which is incorporated herein by reference in its entirety.

STATEMENT REGARDING FEDERALLY SPONSORED RESEARCH OR DEVELOPMENT

Not applicable.

BACKGROUND OF THE INVENTION

1. Field of the Invention

The present invention relates to a method of synthesizing a tetradentate amido macrocyclic ligand and its metal complex.

2. Brief Description of the Related Art

Macrocyclic ligands with various donor atoms are very important to stabilize metals with high valent oxidation states. Such macrocyclic complexes play a significant role in mimicking either structure and/or functions of several metallo enzymes, especially enzymes which use hydrogen peroxides or oxygen for their activity. Amongst many, the development of oxidation resistant stable tetraamido macrocyclic ligand (TAML) developed by Collins and co-workers has drawn much attention in the last two decades or more.

Various metal complexes with unusually high oxidation states using TAMLs have been frequently reported previously by Collins et al. Interestingly, iron complexes of TAMLs (Fe-TAMLs) posses a unique property of activating either hydrogen peroxide or oxygen and act as green oxidation catalysts. Using Fe-TAML and hydrogen peroxide in water, several oxidation chemistries have been demonstrated starting from pollutants remediation associated with the textile, pulp and paper, and pesticides industries to rapidly killing anthrax-like spores and removing sulfur from hydrocarbon fuels. In order to synthesize TAMLs, several synthetic routes have been reported with varying success. In one such instance to synthesize the macrocyclic ligands uses of inorganic or organic azides were encountered, which is not desirable in terms of safety. Coupling of an aromatic diamine and a diacid derivative in a two step process has been utilized; however, yield of ligands using this method is very low.

In recent years an improved synthetic method TAML ligand has been reported. The method uses synthesis of phthalic acid protected amino acid derivatives and then subsequently macrocycle synthesis using several steps. Uffelman and co-workers developed a new synthetic method of making acid chloride of amino acids using phosphorous pentachloride in presence of and reacting with the aromatic amines. Even though over the years easier methods have been developed, synthesis of such macrocyclic ligands needs a much simpler approach.

Several tons of hydrogen peroxide ($H_2O_2$) are annually used for stoichiometric oxidation purposes. The activity of $H_2O_2$ can be enhanced by using various metal complexes. However, the major challenge is to find suitable metal complexes, which can withstand both oxidative stress and also attain high valent metal oxidation states for activity. In this context, a major research effort has evolved over the years focused on the development of metal complexes which mimic structures and/or functions of $H_2O_2$ or oxygen activating metallo-enzymes. Ligands that possess various donor atoms and geometries are very important in order to achieve suitable $H_2O_2$ activating metal complexes or catalysts.

Examples of metal ligand containing bleaching compositions are found in U.S. Pat. Nos. 6,241,779; 6,136,223; 6,099,586; 5,876,625 and 5,853,428, the disclosures of which are incorporated herein be reference. An example of a long-lived homogenous amide containing macrocyclic compounds is found in U.S. Pat. No. 6,054,580, the disclosure of which is incorporated herein by reference.

BRIEF SUMMARY OF INVENTION

To achieve the above objectives, the present invention is directed to a new method of synthesis for a tetradentate amido macrocyclic ligand and its metal complex, resulting in much higher yields. Further, the newly synthesized Fe-complex has been tested as an activator of $H_2O_2$ and found to be very efficient in performing various oxidation chemistries.

BRIEF DESCRIPTION OF THE SEVERAL VIEWS OF THE DRAWINGS

FIG. 7 is a chart listing the turn over numbers and percent yield for pyridine, triethylamine, and 4-dimenthylaminopyridine synthesis.

DETAILED DESCRIPTION OF THE INVENTION

Figure 1:
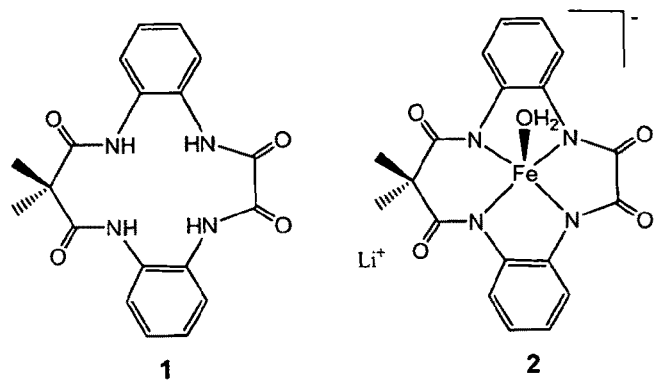
FIG. 1 is the molecular structure of tetradentate amidomacrocyclic ligand and its Fe-complex.

With reference to FIGS. 1-7, the new methodology of synthesizing tetradentate amide based macrocyclic ligand and its iron complex can be described. The molecular structure of tetradentate amide based macrocyclic ligand 1 and its iron complex 2 are shown in FIG. 1. Tetradentate amide based macrocyclic ligand 1 was synthesized using standard reactions of amine and acid chlorides with high yield. Ligand 1 was used to develop its iron complex 2, which is soluble and stable in aqueous solution. Iron complex 2 activates $H_2O_2$ in water under ambient conditions and acts as an excellent oxidation catalyst.

Figure 2:
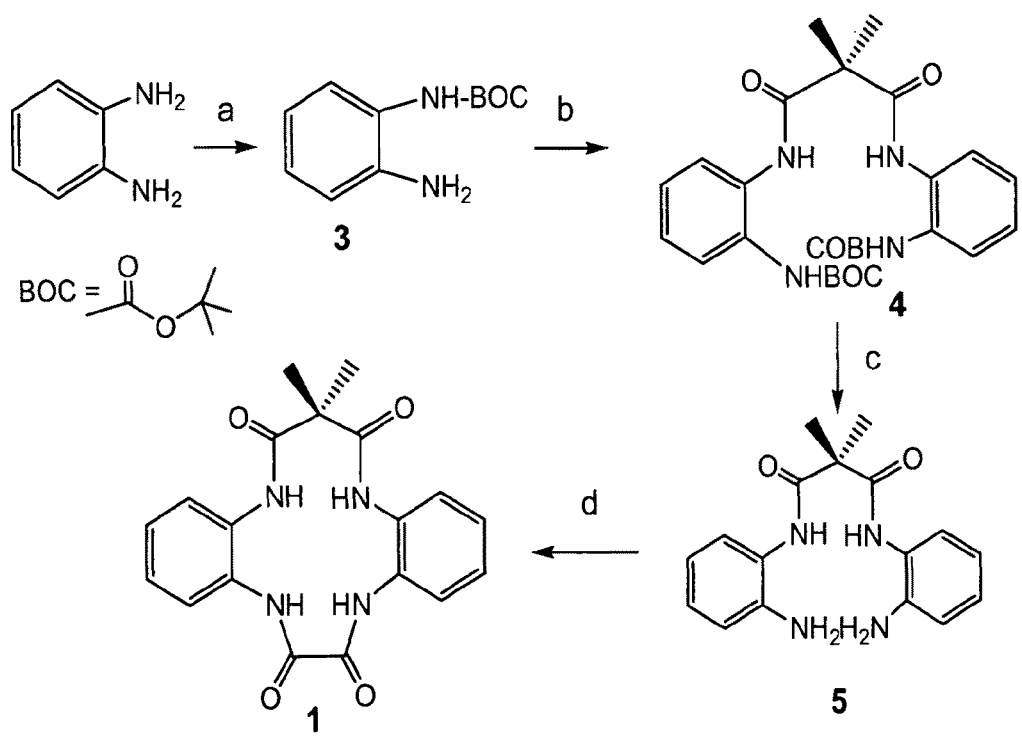
FIG. 2 is the reaction scheme leading to the production of tetradentate amidomacrocyclic ligand.

A new tetradentate amide based macrocyclic ligand 1 and its Fe-complex 2 are synthesized according to FIG. 2. More specifically, O-phenylenediamine (3 gm, 27.8 mmol) and triethylamine (27.8 mmol, 3.8 mL) were dissolved in 47 mL of dry THF (dried over sodium and benzophenone). Di-tert-butyl-carbonate (6.05 gm, 27.8 mmol) was dissolved in 50 mL of THF. Both the solutions were combined in two gas tight syringes separately and added in a three neck round bottom flask containing 50 mL THF via a syringe pump at 0° C. The addition was completed within 16 hours. The reaction mixture was then further stirred at room temperature for another 4 hours. After the reaction, solvent was removed using a rotoevaporator. The residue was dissolved in 200 mL dichloromethane and washed with 5% $Na_2CO_3$ (3×100 mL).

The organic layer was collected and dried using anhydrous sodium sulfate. After filtration, the organic layer was concentrated using a rotoevaporator to yield the slightly yellow product 3. The compound was further purified by recrystallizing from benzene. Initially one of the amine groups of O-phenylenediamine was protected with a tert-butyloxycarbonyl (BOC) group to obtain (2-Amino-phenyl)-carbamic acid tert-butyl ester 3. The stability of the BOC group under basic conditions and its easy removal by acids is of primary advantage for synthesizing the ligand following this method.

Compound 4 was synthesized through a reaction involving (2-Amino-phenyl)-carbamic acid tert-butyl ester 3. More specifically, (2-Amino-phenyl)-carbamic acid tert-butyl ester 3 (2.08 gm, 10 mmol,) was dissolved in 50 mL dry THF. To this solution was added triethylamine (1.4 mL, 10 mmol). The mixture was transferred to a 100 mL two neck round bottom flask and cooled to 0° C. Dimethylmalonyl chloride (1.45 mL, 11 mmol) dissolved in 50 mL dry THF was added into a dropping funnel and the solution was combined slowly for 60 minutes to the other solution drop-wise under nitrogen atmosphere. During the addition, a white precipitate was noted to be formed. The free amine group of (2-Amino-phenyl)-carbamic acid tert-butyl ester 3 reacts with both acid chlorides of dimethylmalonyl chloride to produce compound 4. The reaction proceeds very rapidly in the presence of a triethylamine. Low temperature was maintained since the reaction is an exothermic reaction. After addition of dimethylmalonyl chloride, the reaction mixture was brought to room temperature and stirred overnight under inert atmosphere. After the reaction, the solution was filtered to remove insolubles and filtrate was collected. The residue was dissolved in 200 mL dichloromethane and washed with 5% $Na_2CO_3$ (3×100 mL). The organic layer was collected and dried using anhydrous sodium sulfate. After filtration, the organic layer was concentrated using a rotoevaporator to yield an off-white crude product, compound 4. Following evaporation of the solvent, the product was washed with diethyl ether and dried in vacuum. The compound 4 was further purified by recrystallizing from benzene.

In the next step, the BOC protecting group was removed by treating with trifluoroacetic acid, which occurs within minutes. Compound 4 (1.5 gm, 3.18 mmol) was dissolved in 10 mL dichloromethane and cooled to 0° C. To this solution was added a mixture of trifluoroacetic acid (10 mL) and dichloromethane (20 mL) drop-wise over a period of 30 min under inert atmosphere. After the addition, the reaction mixture was brought to room temperature and stirred for another 2 hours. The reaction mixture then was concentrated using a rotoevaporator to obtain a slightly yellow viscous liquid. This solution was diluted with 75 mL of water and the pH was adjusted with enough 1 M sodium hydroxide solution to bring the pH of the solution to 10 and then extracted with 20 mL of dichloromethane (3×20 mL). The organic layer was dried using anhydrous sodium sulfate. After filtration, the organic layer was concentrated using rotevaporator to yield the white product of compound 5.

For the synthesis of 3, 4 and 5, either washing with dilute mineral acid and/or bases or simple recrystallization from benezene was performed to purify the product with no column chromatography required. Compound 5 (0.408 g, 1.31 mmol) was dissolved in 30 mL dry THF and to the solution was added triethylamine (0.38 mL). The solution was collected in a gas tight syringe. Oxalyl chloride (0.11 mL, 1.31 mmol) was dissolved in 30 mL dry THF and collected in another gas tight syringe. Both solutions were added drop-wise via syringe pump, into a round bottom flask containing 30 mL dry THF that had been cooled to 0° C. and maintained under inert atmosphere. The addition was completed in 16 hours. The mixture was allowed to continue stirring for an additional 4 hours at room temperature. Finally, ligand 1 was synthesized by adding separate solutions of oxalyl chloride and compound 5 in tetrahydrofuran very slowly using a syringe pump. This process is required to reduce other side reactions and maximize macrocycle production. In fact, the structure of 5 may be helpful to some extent in keeping the two amine groups close together which can easily react with oxalyl chloride to form the macrocycle. During the reaction the macrocycle precipitates out from the solution and can be recovered just by simple filtrations. Washing with water was necessary to remove any triethylamine hydrochloride salt which co-precipitates with the ligand during reaction. The resulting product was transferred to a round bottom flask and 200 mL of diethyl ether added. The mixture was sonicated for 15 minutes and then filtered. The precipitate was collected and rinsed with additional ether to further purify the material. The resulting product was dried for 12 hours under vacuum at 80° C. to yield the desired macrocyclic ligand 1. The $^1$H-NMR spectra for all the intermediates including the macrocycle were obtained and indicates the formation of the compounds.

After synthesizing the ligand 1, the Fe-complex 2 was developed. Ligand 1 was first deprotonated using a strong base and reacted with ferrous chloride in dry tetrahydrofuran. More specifically, 1 (200 mg, 0.61 mmol) was dissolved in 30 mL dry THF in a 100 mL Schlenk flask containing a magnetic stir bar and fitted with an $N_2$ gas line. The mixture was cooled to 0° C. using an ice bath. To this mixture was added n-butyllithium (2.56 mmol, 1 mL) and the reaction mixture was stirred for 15 minutes. After stirring for an additional 15 minutes at room temperature, ferrous chloride (85.217 mg, 0.67 mmol) was added and the solution was allowed to stir overnight under $N_2$ atmosphere. During the reaction the mixture turned deep brown. After exposing the reaction mixture to air, the desired Fe(III)-complex 2, which precipitated from the solution, was collected by filtration. The Fe-complex 2 was purified simply by passing through an alumina column.

Figure 3:
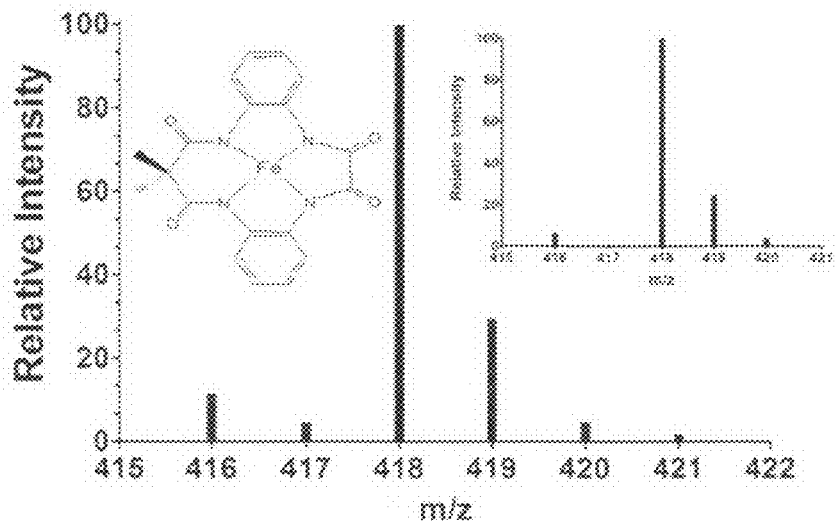
FIG. 3 is the electro spray ionization mass spectrum (ESI-MS) of Fe-Complex (negative ion mode) and its theoretical isotope distribution (inset).

Electro spray ionization mass spectrum (ESI-MS) of the metal complex was obtained and indicates the formation of the metal complex as shown in the FIG. 3. The calculated isotopic distribution is shown in FIG. 3 inset and is in full agreement with the actual isotope distribution observed. The composition of the complex was further verified by elemental analysis which is in agreement with that of desired product. Electrochemical study shows that Fe-complex 2 has two electrochemically reversible peaks at $E_{1/2}$=0.64 V ($E_p$=63 mV) and $E_{1/2}$=0.84 V ($E_p$=77 mV) corresponding to two successive one electron oxidations.

The complex is stable in neutral to alkaline aqueous solutions for several days at moderately high temperature (60-70° C.). However, heating of the aqueous solution of the Fe-complex to 90° C. causes the catalyst to demetallate rapidly as indicated by changes in the UV-Vis spectra. Demetallation gives rise to the free ligand, which was verified by $^1$H-NMR. This is a limitation of using complex 2 at very high temperature. Macrocyclic ring size of thirteen atoms and amide planarity are critical for hydrolytic stability of iron complexes of deprotonated amide ligands. A tetradentate amide ligand with a ring size of fourteen atoms has been reported but the Fe-complex was found to be extremely unstable in water. In the present invention, complex 2 has been synthesized with a ring size of thirteen atoms and the size provides adequate stability to the Fe-complex in aqueous solution.

Figure 4:
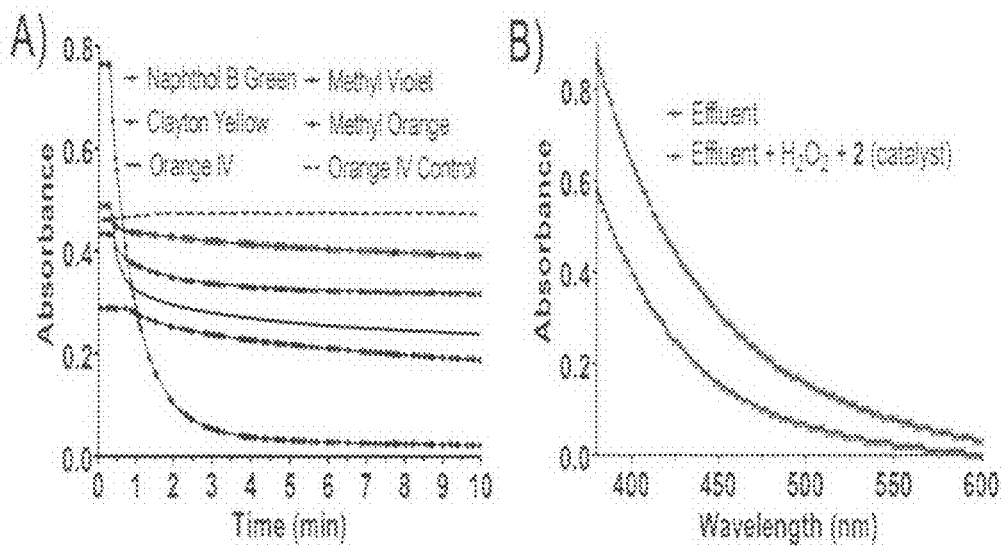
FIG. 4 is a graphical depiction of the change of absorbance as a function of time and wavelength.
Figures 5, 6:
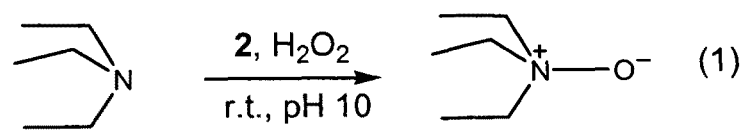
FIG. 5 is a table listing the dyes that were bleached and the time of bleaching at pH 10 and ph 11.5.
FIG. 6 shows the molecular reaction of oxidation of a tertiary amine to its corresponding N-oxide.

The catalytic behavior of the complex as an $H_2O_2$ activator in a variety of oxidation processes is shown in FIGS. 4-5. A working solution of catalyst 2 in $Na_2EDTA$ carbonate/bicarbonate buffer (pH 10) was prepared for use in all reactions. This was done by adding 66.6 μL of a 15,000 ppm EDTA stock solution and 100 μL of a 0.5 mM solution of catalyst 2 to a 100 mL volumetric flask followed by mixing and dilution with 0.1 M carbonate/bicarbonate buffer (pH 10). Final concentrations of EDTA and catalyst 2 were 10 ppm and 0.5 μM respectively. 2980 μL of this working solution was placed in a quartz cuvette fitted with a magnetic stir bar inside. To this solution was added 10 μL of a 3.6 mM purified dye solution (Final dye concentration: 12 μM). The bleaching experiment was initiated by adding 10 μL of 9.4 M $H_2O_2$ to the dye solution in the cuvette yielding a $H_2O_2$ concentration of 31.3 mM. The change of absorbance was monitored as a function of time at the specified wavelengths. Similarly bleaching of all the dyes were also checked using $H_2O_2$ alone at pH 10 and 11.5.

Several water soluble organic dyes were bleached at room temperature in aqueous carbonate/bicarbonate buffer (pH 10) using complex 2 in presence of $H_2O_2$ as primary oxidant. Organic dye (12 μM) and a small amount of catalyst (0.5 μM) were combined in buffer solution and the reaction was initiated by adding $H_2O_2$ (3 mM). A small amount of sodium salt of ethylenediamine tetraacetate (EDTA) was added into the reaction mixture to remove any free transition metal ion in the solution and thus minimize hydroxyl radical dominated chemistry. FIG. 4A shows the bleaching of several dyes at room temperature. FIG. 5 shows the list of dyes which were bleached using complex 2. $\lambda_{max}$ was the wavelength used to determine bleaching time. Bleaching time is defined to be the time at which both A≤half of initial value and the slope of A vs time curve approaches zero for a chosen $\lambda_{max}$. All the reactions were performed in pH 10 or 11.5 carbonate buffer with 10 ppm EDTA, dye concentration of 12 μM, $H_2O_2$ concentration 31.3 mM, and catalyst 2 concentration of 0.5 μM at 25° C. Methyl Violet, Clayton Yellow, Orange IV, Napthol B green were bleached rapidly. However, the bleaching of Methyl Orange was very slow. $H_2O_2$ alone when tested to bleach the dyes under similar conditions was found to be much slower in bleaching the dyes. FIG. 4A shows the bleaching of Orange IV in presence of $H_2O_2$ at pH 10 which shows practically no bleaching of dyes. The catalyst however becomes inactivated after a certain time and bleaching is not as effective as previously reported with Fe-TAML catalysts. The bleaching experiment was also done at pH 11.5 and testing did not show any difference in activity compared to experiments at pH 10.

The ability of the catalysts to remove color from pulp and paper effluent along with $H_2O_2$ under ambient conditions was also determined. The pH of the effluent was adjusted to 9.5 using concentrated sodium hydroxide solution. To 100 mL of the effluent solution was added 600 μL 2.17 mM solution of catalyst 2. 300 μL 9.4 M hydrogen peroxide was added to this solution and stirred at room temperature for 4 hours. As a control, to another 100 mL effluent solution, was added 300 μL 9.4 M hydrogen peroxide that was also stirred for 4 hours at room temperature. The solutions were diluted and absorbances of the solutions were measured and compared to the unbleached solutions. Absorbances at 466 nm were recorded and used to calculate color disappearance. FIG. 4B revealed that catalyst 2 (13 μM; 6 mg catalyst/L effluent) can remove 52% color (calculated using absorbance at 466 nm) of the effluent within 4 hours at pH 9.5. $H_2O_2$ itself can also remove color under similar reaction conditions although bleaching is less (30%).

FIG. 6 shows the oxidization of a tertiary amine to its corresponding N-oxides, which have tremendous usefulness both in synthetic and biological applications. The reactions were carried out at pH 10 using catalyst 2 and $H_2O_2$ at room temperature. The reactions show turn over numbers of 667 with very good yields of N-oxides. For comparison, amines were also oxidized with only hydrogen peroxide. The N-oxides (products) and reactants (amines) were checked after the reaction either by GC/MS or ESI-MS. Pyridine (0.05 mL, 0.620 mmol) was added to 1 mL 0.1 M carbonate/bicarbonate buffer. To this solution was added 0.34 mL of 9.4 M hydrogen peroxide (3.10 mmol) and 0.36 mL of $2.15 \times 10^{-3}$ M of catalyst 2 (0.775 μmol). The solution was stirred at room temperature for 2 hours. An aliquot of the solution was added to acetonitrile, filtered and analyzed by GC/MS to check the N-oxide of pyridine. Product formation was checked by LC/MS too. No other detectable product was observed under the reaction condition. Quantification of product was performed by checking the disappearance of pyridine by GC/MS. As shown in FIG. 7, a turn over number (TON=Moles of product formed/moles of catalyst) of 407 was observed for pyridine-N-oxide synthesis. Under the reaction conditions, 50.8% yield of product was obtained. When hydrogen peroxide alone was used, only 20% yield was obtained under similar conditions. In case of trienthylamine, a higher TON of 667 was obtained with 66.67% yield. 4-Dimethylaminopyridine was also used for the reaction. Corresponding N-oxide formation was checked by mass spectrometer but not quantified.

The Fe-Complex may be used as an activator of hydrogen peroxide for oxidation purposes, including without limitation, (a) pulp and paper effluent bleaching, (b) dye bleaching, and (c) small molecule synthesis by oxidation (e.g. N-oxides, epoxides, aldehydes and the like may be synthesized from the oxidation of suitable precursor molecules).

The present invention has been described with reference to certain preferred and alternative embodiments that are intended to be exemplary only and not limiting to the full scope of the present invention as set forth in the appended claims.

What is claimed is:

1. A tetradentate amido macrocycle ligand made by a process comprising the steps of:
    (a) protecting one of the amine groups of o-phenylenediamine with a tert-butyloxycarbonyl group (BOC);
    (b) reacting the product of step (a) with dimethylmalonyl chloride in the presence of triethylamine;
    (c) reacting the product of step (b) with triflouroacetic acid to remove the protecting BOC group; and
    (d) reacting the product of step (c) with oxalyl chloride in the presence of triethylamine to produce a tetradentate amido macrocycle ligand.

2. A process for synthesizing a tetradentate amido macrocyclic ligand, comprising the steps of:
    (a) protecting one of the amine groups of o-phenylenediamine with a tert-butyloxycarbonyl group (BOC);
    (b) reacting the product of step (a) with dimethylmalonyl chloride in the presence of triethylamine;
    (c) reacting the product of step (b) with triflouroacetic acid to remove the protecting BOC group; and
    (d) reacting the product of step (c) with oxalyl chloride in the presence of triethylamine to produce a tetradentate amido macrocycle ligand.

3. A process for synthesizing an iron complex of the tetradentate amido macrocyclic ligand produced by the method of claim 2, comprising the steps of:
    deprotonating the ligand of claim 2 with a strong base, reacting the resulting product with ferrous chloride and exposing the resulting mixture to air.

4. An iron complex of a tetradentate amido macrocycle ligand made by the process of claim 3.

5. A process of using the iron complex of claim 4 for an activator of hydrogen peroxide for oxidation of a substrate, comprising the step of contacting the substrate with the iron complex of claim 4 and hydrogen peroxide.

6. The process of claim 5, wherein said substrate comprises pulp and paper effluent.

7. The process of claim 5, wherein said substrate comprises a dye.

8. The process of claim 5, wherein said substrate is selected from precursor molecules from which small molecules are synthesized by oxidation.

* * * * *